(12) United States Patent
Elworthy et al.

(10) Patent No.: US 7,947,709 B2
(45) Date of Patent: May 24, 2011

(54) NON-NUCLEOSIDE REVERSE TRANSCRIPTASE INHIBITORS

(75) Inventors: Todd Richard Elworthy, Los Altos, CA (US); Joan Heather Hogg, Sunnyvale, CA (US); Joshua Kennedy-Smith, San Francisco, CA (US); Counde O'Yang, Sunnyvale, CA (US); Mark Smith, San Francisco, CA (US); Zachary Kevin Sweeney, Redwood City, CA (US); Jeffrey Wu, Saratoga, CA (US)

(73) Assignee: Roche Palo Alto LLC, South San Francisco, CA (US)

( * ) Notice: Subject to any disclaimer, the term of this patent is extended or adjusted under 35 U.S.C. 154(b) by 280 days.

(21) Appl. No.: 12/214,651

(22) Filed: Jun. 20, 2008

(65) Prior Publication Data

US 2009/0012034 A1    Jan. 8, 2009

Related U.S. Application Data

(60) Provisional application No. 60/936,956, filed on Jun. 22, 2007.

(51) Int. Cl.
    A61K 31/708      (2006.01)
    A61K 31/4184     (2006.01)
    A61K 31/437      (2006.01)
    A61K 31/5025     (2006.01)
    A61P 31/18       (2006.01)
    C07D 235/26      (2006.01)
    C07D 471/04      (2006.01)
    C07D 487/04      (2006.01)

(52) U.S. Cl. .......... 514/303; 514/388; 514/45; 514/395; 514/248; 546/123; 546/118; 548/306.4; 544/236

(58) Field of Classification Search ................. 514/303, 514/388; 546/123; 548/306.4
    See application file for complete search history.

(56) References Cited

U.S. PATENT DOCUMENTS

| | | |
|---|---|---|
| 7,166,738 B2 | 1/2007 | Dunn et al. |
| 7,189,718 B2 | 3/2007 | Dunn et al. |
| 7,208,509 B2 | 4/2007 | Dunn et al. |
| 2005/0215554 A1 | 9/2005 | Dunn et al. |
| 2005/0239880 A1 | 10/2005 | Dunn et al. |
| 2006/0025462 A1 | 2/2006 | Dunn et al. |
| 2006/0069261 A1 | 3/2006 | Bonneau et al. |
| 2006/0223874 A1 | 10/2006 | Martin et al. |
| 2007/0078128 A1 | 4/2007 | Saito et al. |
| 2007/0088015 A1 | 4/2007 | Silva et al. |
| 2007/0088053 A1 | 4/2007 | Mirzadegan et al. |
| 2008/0020981 A1 | 1/2008 | Sweeney |

FOREIGN PATENT DOCUMENTS

| | | | |
|---|---|---|---|
| WO | WO 02/04424 A1 | 1/2002 | |
| WO | WO 02/085860 A1 | 10/2002 | |
| WO | WO 02/100853 A1 | 12/2002 | |
| WO | WO 2004/029042 A1 | 4/2004 | |
| WO | WO 2004/029051 A1 | 4/2004 | |
| WO | WO 2004/031178 A1 | 4/2004 | |
| WO | WO 2006014136 A1 * | 2/2006 | |
| WO | WO 2006/067587 A2 | 6/2006 | |
| WO | WO 2006/067587 A3 | 6/2006 | |
| WO | WO 2007/015809 A2 | 2/2007 | |
| WO | WO 2008/009613 A1 | 1/2008 | |

OTHER PUBLICATIONS

Wikipedia, treating HIV and AIDS_2010_p. 1-2.*
Chan, J. H., wt. al. "Novel Benzophenones as Non-nucleoside Reverse Transcriptase Inhibitors of HIV-1," *J. Med. Chem.* 2004, vol. 47, pp. 1175-1182.
Genin M. J., et. al. Novel 1,5-Diphenylpyrazole Nonnucleoside HIV-1 Reverse Transcriptase Inhibitors with Enhanced Activity versus the Delavirdine-Resistant P236L Mutant : Lead Identification and SAR of 3- and 4-Substituted Derivatives, *J. Med. Chem.* 2000, vol. 43, pp. 1034-1040.
Romines, K. R. et. al. "Structure-Activity Relationship Studies of Novel Benzophenones Leading to the Discovery of a Potent, Next Generation HIV Non-nucleoside Reverse Transcriptase Inhibitors," *J. Med. Chem.*2006, vol. 49, pp. 727-739.
Wyatt, P. G., et. al. Benzophenone Derivatives : A Novel Series of Potent and Selective Inhibitors of Human Immunodeficiency Virus Type 1 Reverse Transcriptase, *J. Med. Chem.* 1995 vol. 38, pp. 1657-1665.

* cited by examiner

*Primary Examiner* — Yong Chu
(74) *Attorney, Agent, or Firm* — Brian L. Buckwalter

(57) ABSTRACT

Compounds of formula I, wherein $R^1$, $R^2$, $R^3$, X and Ar, are as defined herein or pharmaceutically acceptable salts thereof, inhibit HIV-1 reverse transcriptase and afford a method for prevention and treatment of HIV-1 infections and the treatment of AIDS and/or ARC. The present invention also relates to compositions containing compounds of formula I useful for the prevention and treatment of HIV-1 infections and the treatment of AIDS and/or ARC.

(I)

11 Claims, No Drawings

```
                         SEQUENCE LISTING

<160> NUMBER OF SEQ ID NOS: 2

<210> SEQ ID NO 1
<211> LENGTH: 47
<212> TYPE: RNA
<213> ORGANISM: Artificial sequence
<220> FEATURE:
<223> OTHER INFORMATION: sequence is synthesized

<400> SEQUENCE: 1
gggucucucu gguuagacca cucuagcagu ggcgcccgaa  cagggac                47

<210> SEQ ID NO 2
<211> LENGTH: 18
<212> TYPE: DNA
<213> ORGANISM: Artificial sequence
<220> FEATURE:
<223> OTHER INFORMATION: sequence is synthesized

<400> SEQUENCE: 2
gtccctgttc  gggcgcca                                                18
```

NON-NUCLEOSIDE REVERSE TRANSCRIPTASE INHIBITORS

CROSS REFERENCE TO PRIOR APPLICATIONS

The application claims the benefit of priority to U.S. Provisional Application No. 60/936,956 filed Jun. 22, 2007 and contents of which is incorporated by reference in its entirety.

FIELD OF THE INVENTION

The invention relates to the field of antiviral therapy and, in particular, to non-nucleoside compounds that inhibit HIV-1 reverse transcriptase and are useful for treating Human Immunodeficiency Virus (HIV-1) mediated diseases. The invention provides novel urea and carbamate derivatives to formula I, for treatment or prophylaxis of HIV-1 mediated diseases, AIDS or ARC, employing said compounds in monotherapy or in combination therapy.

BACKGROUND OF THE INVENTION

The invention relates to the field of antiviral therapy and, in particular, to non-nucleoside compounds that inhibit HIV-1 reverse transcriptase and are useful for treating Human Immunodeficiency Virus (HIV-1) mediated diseases. The invention provides novel ureas and heterocyclic compounds according to formula I, for treatment or prophylaxis of HIV-1 mediated diseases, AIDS or ARC, employing said compounds in monotherapy or in combination therapy.

The human immunodeficiency virus HIV-1 is the causative agent of acquired immunodeficiency syndrome (AIDS), a disease characterized by the destruction of the immune system, particularly of the CD4+ T-cell, with attendant susceptibility to opportunistic infections. HIV-1 infection is also associated with a precursor AIDS-related complex (ARC), a syndrome characterized by symptoms such as persistent generalized lymphadenopathy, fever and weight loss.

In common with other retroviruses, the HIV genome encodes protein precursors known as gag and gag-pol which are processed by the viral protease to afford the protease, reverse transcriptase (RT), endonuclease/integrase and mature structural proteins of the virus core. Interruption of this processing prevents the production of normally infectious virus. Considerable efforts have been directed towards the control of HIV by inhibition of virally encoded enzymes.

Two enzyme have been extensively studied for HIV-1 chemotherapy: HIV-1 protease and HIV-1 reverse transcriptase. (J. S. G. Montaner et al., *Biomed & Pharmacother.* 1999 53:63-72; R. W. Shafer and D. A. Vuitton, *Biomed. & Pharmacother.* 1999 53:73-86; E. De Clercq, *Curr. Med. Chem.* 2001 8:1543-1572). Two general classes of RTI inhibitors have been identified: nucleoside reverse transcriptase inhibitors (NRTI) and non-nucleoside reverse transcriptase inhibitors (NNRTI). Currently the CCR5 co-receptor has emerged as a potential target for anti-HIV-1 chemotherapy (D. Chantry, *Expert Opin. Emerg. Drugs* 2004 9(1):1-7; C. G. Barber, *Curr. Opin. Invest. Drugs* 2004 5(8):851-861; D. Schols, *Curr. Topics Med. Chem.* 2004 4(9):883-893; N. A. Meanwell and J. F. Kadow, *Curr. Opin. Drug Discov. Dev.* 2003 6(4):451-461).

A third enzyme integrase also is under active investigation. N-substituted hydroxy pyrimidinone carboxamide inhibitors of HIV-1 integrase inhibitors have been disclosed by B. Crescenzi et al. in WO2003/035077, published May 1, 2003, and MK-0518 (raltegravir) has been approved by the FDA. GS 9137 (Elvitegravir) or JTK-303, licensed by Gilead Sciences from Japan Tobacco is undergoing Phase 2 trials. (A. Savarino A. *Expert Opin Investig Drugs.* 2006 15(12):1507-22)

NRTIs typically are 2',3'-dideoxynucleoside (ddN) analogs which must be phosphorylated prior to interacting with viral RT. The corresponding triphosphates function as competitive inhibitors or alternative substrates for viral RT. After incorporation into nucleic acids the nucleoside analogs terminate the chain elongation process. HIV-1 reverse transcriptase has DNA editing capabilities which enable resistant strains to overcome the blockade by cleaving the nucleoside analog and continuing the elongation.

NNRTIs were first discovered in 1989. NNRTI are allosteric inhibitors which bind reversibly at a nonsubstrate-binding site on the HIV-1 reverse transcriptase thereby altering the shape of the active site or blocking polymerase activity (R. W. Buckheit, Jr., *Expert Opin. Investig. Drugs* 2001 10(8)1423-1442; E. De Clercq, *Antiviral Res.* 1998 38:153-179; E. De Clercq, *Current Med. Chem.* 2001 8(13):1543-1572; G. Moyle, 2001 61 (1):19-26). Although over thirty structural classes of NNRTIs have been identified in the laboratory, only four compounds have been approved for HIV-1 therapy: efavirenz, nevirapine, delavirdine and etravirine.

Initially viewed as a promising class of compounds, in vitro and in vivo studies quickly revealed the NNRTIs presented a low barrier to the emergence of drug resistant HIV-1 strains and class-specific toxicity. Drug resistance frequently develops with only a single point mutation in the RT. While combination therapy with NRTIs, PIs and NNRTIs has, in many cases, dramatically lowered viral loads and slowed disease progression, significant therapeutic problems remain. (R. M. Gulick, *Eur. Soc. Clin. Microbiol. and Inf. Dis.* 2003 9(3): 186-193) The cocktails are not effective in all patients, potentially severe adverse reactions often occur and the rapidly reproducing HIV-1 virus has proven adroit at creating mutant drug-resistant variants of wild type protease and reverse transcriptase. There remains a need for safer drugs with activity against wild type and commonly occurring resistant strains of HIV-1.

Pyridazinone non-nucleoside reverse transcriptase inhibitors have been described by J. P. Dunn et al. in U.S. Pat. No. 7,189,718 issued Mar. 13, 2007 and by J. P. Dunn et al. in U.S. Publication No. 2005021554 filed Mar. 22, 2005. 5-Aralkyl-2,4-dihydro-[1,2,4]triazol-3-one, 5-aralkyl-3H-[1,3,4]oxadiazol-2-one and 5-aralkyl-3H-[1,3,4]thiadiazol-2-one non-nucleoside reverse transcriptase inhibitors have been disclosed by J. P. Dunn et al. in U.S. Pat. No. 7,208,059 issued Apr. 24, 2007, U.S. Patent Publication 20060225874 published Oct. 5, 2006 and U. S. Publication No. 20060025462 filed Jun. 27, 2005. Related compounds are disclosed by Y. D. Saito et al. in U. S. Publication No. 20070078128 published Apr. 5, 2007. Phenylacetamide non-nucleoside reverse transcriptase inhibitors have been disclosed by J. P. Dunn et al. in U.S. Pat. No. 7,166,738 issued Jan. 23, 2007 and methods for treating retroviral infection with phenylacetamide compounds have been disclosed by J. P. Dunn et al. in U. S. Publication No. 20050239880 published Oct. 27, 2005; T. Mirzadegan and T. Silva in U. S. Publication No. 20070088053 published Apr. 19, 2007; and by Z. K. Sweeney and T. Silva in U. S. Publication No. 20070088015 published Apr. 19, 2007. These applications are hereby incorporated by reference in their entirety.

In WO2006/067587 published Jun. 26, 2006, L. H. Jones et al. disclose phenoxyacetamide derivatives and compositions containing them which bind HIV-1 reverse transcriptase and are modulators, especially inhibitors, thereof. K. R. Romines et al (*J. Med. Chem.* 2006 49(2):727-739) and P. Bonneau et al. (U.S. Publication No. 20060069261 published Mar. 30, 2006) describe phenoxyacetamides that inhibit HIV-1 reverse transcriptase. In U. S. Patent Publication 2007/0021442 published Jan. 25, 2007, S. A. Saggar et al. disclose diphenyl ether HIV-1 reverse transcriptase inhibitors.

SUMMARY OF THE INVENTION

The present invention relates to a compound according to formula I wherein:

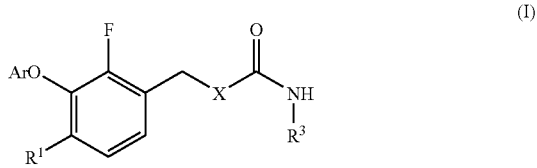

X is O or $NR^2$;

$R^1$ is halogen, $C_{1-6}$ alkyl, $C_{3-7}$ cycloalkyl, $C_{1-6}$ haloalkyl, or $C_{1-6}$ alkoxy;

$R^2$ and $R^3$ independently are (i) hydrogen or $C_{1-6}$ alkyl; (ii) $R^2$ and $R^3$ together are $(CH_2)_n$, ortho-phenylene, pyridinylene, 3,4-pyridazylene or CH=N wherein n is an integer from 2 to 4 and a nitrogen atom in said pyridinylene or 3,4-pyridazylene ring can be optionally be substituted with an oxygen; or, (iii) $R^2$ is hydrogen and $R^3$ is phenyl optionally substituted with one to 3 substituents optionally selected from the group consisting of $C_{1-6}$ alkyl, $C_{1-6}$ haloalkyl, $C_{1-6}$ alkoxy, $C_{1-6}$ haloalkoxy, halogen, cyano and nitro;

Ar is phenyl optionally substituted with 1-3 groups independently selected from the group consisting of selected from halogen, cyano, $C_{1-6}$ haloalkyl and $C_{1-6}$ alkyl; or, a pharmaceutically acceptable salts thereof.

Compounds of formula I inhibit HIV-1 reverse transcriptase and afford a method for prevention and treatment of HIV-1 infections and the treatment of AIDS and/or ARC. HIV-1 undergoes facile mutations of its genetic code resulting in strains with reduced susceptibility to therapy with current therapeutic options. The present invention also relates to compositions containing compounds of formula I useful for the prevention and treatment of HIV-1 infections and the treatment of AIDS and/or ARC. The present invention further relates to compounds of formula I which are useful in monotherapy or combination therapy with other anti-viral agents.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The phrase "optional bond" means that the bond may or may not be present, and that the description includes single, double, or triple bonds. If a substituent is designated to be a "bond" or "absent", the atoms linked to the substituents are then directly connected.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

A "stable" compound is a compound which can be prepared and isolated and whose structure and properties remain or can be made to remain essentially unchanged for a period of time sufficient to allow the use of the compound for the purposes described herein (e.g., therapeutic or prophylactic administration to a subject).

Unless expressly stated to the contrary, all ranges cited herein are inclusive. For example, a heterocyclic ring described as containing "1 to 4 heteroatoms" means the ring can contain 1, 2, 3 or 4 heteroatoms. It is also to be understood that any range cited herein includes within its scope all of the subranges within that range. Thus, for example, an aryl or a heteroaryl described as optionally substituted with "from 1 to 5 substituents" is intended to include as aspects thereof, any aryl optionally substituted with 1 to 4 substituents, 1 to 3 substituents, 1 to 2 substituents, 2 to 5 substituents, 2 to 4 substituents, 2 to 3 substituents, 3 to 5 substituents, 3 to 4 substituents, 4 to 5 substituents, 1 substituent, 2 substituents, 3 substituents, 4 substituents, and 5 substituents.

The symbol "*" at the end of a bond or " ------- " drawn through a bond each refer to the point of attachment of a functional group or other chemical moiety to the rest of the molecule of which it is a part. Thus, for example:

MeC(=O)OR⁴ wherein

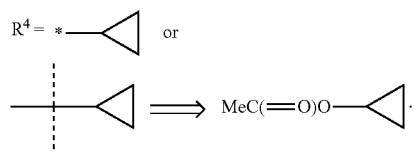

It is contemplated that the definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe— or —CH$_2$CH(i-Pr)CH$_2$—), unless otherwise indicated. The open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "haloalkyl" as used herein denotes an unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "haloalkoxy" as used herein refers to a group —OR where R is haloalkyl as defined herein. The term "haloalkylthio" as used herein refers to a group —SR where R is haloalkyl as defined herein.

The term "halogen" or "halo" as used herein means fluorine, chlorine, bromine, or iodine.

The terms ortho-phenylene, 2,3-pyrindinylene, 3,4-pyridinylene or 3,4-pyridazylene as used herein refer to the moieties (i) to (iv) respectively. 2,4-dihydro-[1,2,4]triazol-3-one as used herein refers to (v). The diaryl ether is linked to the nitrogen at C-3 of ii and iii and C4 of iv. The nitrogen atom of the pyridine rings or one nitrogen atom of the pyridazine ring is optionally substituted with an oxygen atom to form a nitrogen N-oxide. Preparation of N-oxides is well known and may be carried out, for example, in a suitable organic solvent (dichloromethane, chloroform, benzene, hexane or t-butanol, etc.) in the presence of an excess of oxidizing agent (e.g., sodium peroxide, hydrogen peroxide, sodium periodate, acyl nitrite, sodium perborate, meta-chloroperbenzoic acid or other peracid, OXONE®(potassium peroxymonosulfate), potassium permanganate or chromic acid) typically at temperatures from 20-60° C.

i

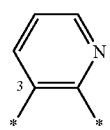

ii

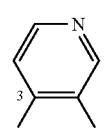

iii

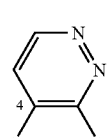

iv

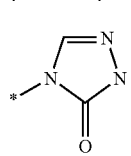

v

The term urea as used herein refers to a compound containing a R'R"N(=O)NHR''' wherein R" and R''' are optional an alkylene chain which may be saturated or fused to a phenyl, pyridinyl or pyridazinyl ring. The R' residue is a methylene linked to a bis-aryl ether. The term carbamate as used herein refers to a compound containing a R'OC(=O)NHR'''.

In one embodiment of the present invention there is provided a compound according to formula I wherein $R^1$, $R^2$, $R^3$, X and Ar are as defined herein above. In all other embodiments provided below, substituents which can be present in each embodiment and which are not explicitly defined retain the broadest definition provided in the Summary of the Invention.

In a second embodiment of the present invention there is provided a compound according to formula I wherein X is $NR^2$.

In a third embodiment of the present invention there is provided a compound according to formula I wherein X is $NR^2$ and $R^2$ and $R^3$ together are ortho-phenylene, pyridinylene or 3,4-pyridazylene.

In a fourth embodiment of the present invention there is provided a compound according to formula I wherein X is $NR^2$; $R^2$ and $R^3$ together are ortho-phenylene, pyridinylene or 3,4-pyridazylene; $R^1$ is bromo, chloro or $C_{1-6}$ alkyl; and Ar is a 3,5-disubstituted phenyl moiety wherein the substituents are selected from halogen, cyano, $C_{1-6}$ haloalkyl or $C_{1-6}$ alkyl In a fifth embodiment of the present invention there is provided a compound according to formula I wherein X is $NR^2$; $R^2$ and $R^3$ together are ortho-phenylene, pyridinylene or 3,4-pyridazylene; $R^1$ is bromo, chloro or $C_{1-6}$ alkyl; and Ar is 3-chloro-5-cyano-phenyl, 3,5-dicyano-phenyl or 3-cyano-5-difluoromethyl-phenyl.

In a sixth embodiment of the present invention there is provided a compound according to formula I wherein X is $NR^2$; $R^2$ and $R^3$ together are 2,3- or 3,4-pyridinylene; $R^1$ is bromo, chloro or $C_{1-6}$ alkyl; and Ar is 3-chloro-5-cyano-phenyl, 3,5-dicyano-phenyl or 3-cyano-5-difluoromethyl-phenyl.

In a seventh embodiment of the present invention there is provided a compound according to formula I wherein X is $NR^2$; $R^2$ and $R^3$ together are 3,4-pyridazylene; $R^1$ is bromo, chloro or $C_{1-6}$ alkyl; and Ar is 3-chloro-5-cyano-phenyl, 3,5-dicyano-phenyl or 3-cyano-5-difluoromethyl-phenyl.

In a eighth embodiment of the present invention there is provided a compound according to formula I wherein X is $NR^2$; $R^2$ and $R^3$ together with the atoms to which thy are attached form a 2,4-dihydro-[1,2,4]triazol-3-one; $R^1$ is bromo, chloro or $C_{1-6}$ alkyl; and Ar is a 3,5-disubstituted phenyl moiety wherein the substituents are selected from halogen, cyano, $C_{1-6}$ haloalkyl or $C_{1-6}$ alkyl.

In a ninth embodiment of the present invention there is a compound selected from 3-[6-bromo-2-fluoro-3-(2-oxo-2,3-dihydro-benzoimidazol-1-ylmethyl)-phenoxy]-5-chloro-benzonitrile; 3-[6-bromo-2-fluoro-3-(2-oxo-2,3-dihydro-imidazo[4,5-b]pyridin-1-ylmethyl)-phenoxy]-5-chloro-benzonitrile; 3-[6-bromo-2-fluoro-3-(2-oxo-2,3-dihydro-imidazo[4,5-c]pyridin-1-ylmethyl)-phenoxy]-5-chloro-benzonitrile; 3-chloro-5-[6-chloro-2-fluoro-3-(2-oxo-2,3-dihydro-imidazo[4,5-c]pyridin-1-ylmethyl)-phenoxy]-benzonitrile; or, 3-[6-bromo-2-fluoro-3-(6-oxo-6,7-dihydro-imidazo[4,5-c]pyridazin-5-ylmethyl)-phenoxy]-5-chloro-benzonitrile.

In a tenth embodiment of the present invention there is provided a method for treating an HIV-1 infection, or preventing an HIV-1 infection, or treating AIDS or ARC, comprising administering to a host in need thereof a therapeutically effective amount of a compound according to formula I wherein $R^1$, $R^2$, $R^3$, X and Ar are as defined herein above.

In a eleventh embodiment of the present invention there is provided a method for treating an HIV-1 infection, or preventing an HIV-1 infection, or treating AIDS or ARC, comprising co-administering to a host in need thereof a therapeutically effective amount of a compound according to formula I wherein $R^1$, $R^2$, $R^3$, X and Ar are as defined herein above and at least one compound selected from the group consisting of HIV protease inhibitors, nucleoside reverse transcriptase inhibitors, non-nucleoside reverse transcriptase inhibitors, integrase inhibitors, CCR5 antagonists and viral fusion inhibitors.

In a twelfth embodiment of the present invention there is provided a method for treating an HIV-1 infection, or preventing an HIV-1 infection, or treating AIDS or ARC, comprising co-administering to a host in need thereof a therapeutically effective amount of a compound according to formula I wherein $R^1$, $R^2$, $R^3$, X and Ar are as defined herein and at least one compound selected from the group zidovudine, lamivudine, didanosine, zalcitabine, stavudine, rescriptor, sustiva viramune, efavirenz, nevirapine or delavirdine, saquinavir, ritonavir, nelfinavir, indinavir, amprenavir, lopinavir, raltegravir potassium and enfuvirtide.

In a thirteenth embodiment of the present invention there is provided a method for inhibiting HIV-1 reverse transcriptase in a host infected with HIV-1 comprising administering a therapeutically effective amount of a compound according to comprising administering to a host in need thereof a therapeutically effective amount of a compound according to formula I wherein $R^1$, $R^2$, $R^3$, X and Ar are as defined herein above.

In a fourteenth embodiment of the present invention there is provided a method for inhibiting HIV-1 reverse transcriptase in a host infected with HIV-1 expressing a reverse transcriptase with at least one mutation compared to wild type HIV-1 comprising administering a therapeutically effective amount of a compound according to comprising administering to a host in need thereof a therapeutically effective amount of a compound according to formula I wherein $R^1$, $R^2$, $R^3$, X and Ar are as defined herein above.

In a fifteenth embodiment of the present invention there is provided a method for inhibiting HIV-1 reverse transcriptase in a host infected with HIV-1 expressing a reverse transcriptase exhibiting reduced susceptibility to efavirenz, nevirapine or delavirdine comprising administering a therapeutically effective amount of a compound according to comprising administering to a host in need thereof a therapeutically effective amount of a compound according to formula I wherein $R^1$, $R^2$, $R^3$, X and Ar and n are as defined herein above.

In a sixteenth embodiment of the present invention there is provided a pharmaceutical composition comprising a therapeutically effective amount of a compound according to comprising administering to a host in need thereof a therapeutically effective amount of a compound according to formula I wherein $R^1$, $R^2$, $R^3$, X and Ar and n are as defined herein above and at least on carrier, excipient or diluent.

A-M. Vandamme et al. (*Antiviral Chemistry & Chemotherapy*, 1998 9:187-203) disclose current HAART clinical treatments of HIV-1 infections in man including at least triple drug combinations. Highly active anti-retroviral therapy (HAART) has traditionally consisted of combination therapy with nucleoside reverse transcriptase inhibitors (NRTI), non-nucleoside reverse transcriptase inhibitors (NNRTI) and protease inhibitors (PI). These compounds inhibit biochemical processes required for viral replication. While HAART has dramatically altered the prognosis for HIV-1 infected persons, there remain many drawbacks to the current therapy including highly complex dosing regimes and side effects which can be very severe (A. Carr and D. A. Cooper, *Lancet* 2000 356(9239):1423-1430). Moreover, these multidrug therapies do not eliminate HIV-1 and long-term treatment usually results in multidrug resistance, thus limiting their utility in long term therapy. Development of new therapeutics which can be used in combination with NRTIs, NNRTIs, PIs and viral fusion inhibitors to provide better HIV-1 treatment remains a priority.

Typical suitable NRTIs include zidovudine (AZT; RETROVIR®); didanosine (ddl; VIDEX®); zalcitabine (ddC; HIVID®); stavudine (d4T; ZERIT®); lamivudine (3TC; EPIVIR®); abacavir (ZIAGEN®); adefovir dipivoxil [bis(POM)-PMEA; PREVON®] and tenofovir (VIREAD, TDF or PMPA); lobucavir (BMS-180194), a nucleoside reverse transcriptase inhibitor disclosed in EP-0358154 and EP-0736533; BCH-10652, a reverse transcriptase inhibitor (in the form of a racemic mixture of BCH-10618 and BCH-10619) under development by Biochem Pharma; emitricitabine [(−)-FTC] in development by Triangle Pharmaceuticals; β-L-FD4 (also called β-L-D4C and named β-L-2', 3'-dicleoxy-5-fluoro-cytidene) licensed Vion Pharmaceuticals; DAPD, the purine nucleoside, (−)-β-D-2,6-diamino-purine dioxolane disclosed in EP-0656778 and licensed to Triangle Pharmaceuticals; and lodenosine (FddA), 9-(2,3-dideoxy-2-fluoro-β-D-threo-pentofuranosyl)adenine, an acid stable purine-based reverse transcriptase inhibitor under development by U.S. Bioscience Inc.

Typical suitable NNRTIs include nevirapine (BI-RG-587; VIRAMUNE®); delaviradine (BHAP, U-90152; RESCRIPTOR®); efavirenz (DMP-266; SUSTIVA®); PNU-142721, a furopyridine-thio-pyrimidine under development by Pfizer; AG-1549 (formerly Shionogi # S-1153); 5-(3,5-dichlorophenyl)-thio-4-isopropyl-1-(4-pyridyl)methyl-1H-imidazol-2-ylmethyl carbonate disclosed in WO 96/10019; MKC442 (1-(ethoxy-methyl)-5-(1-methylethyl)-6-(phenylmethyl)-(2, 4(1H, 3H)-pyrimidinedione); and (+)-calanolide A (NSC-675451) and B, coumarin derivatives disclosed in U.S. Pat. No. 5,489,697.

Typical suitable PIs include saquinavir (Ro 31-8959; INVIRASE®; FORTOVASE®); ritonavir (ABT-538; NORVIR®); indinavir (MK-639; CRIXIVAN®); nelfnavir (AG-1343; VIRACEPT®); amprenavir (141W94; AGENERASE®); TMC114 (darunavir, PREZISTA®); lasinavir (BMS-234475); DMP-450, a cyclic urea under development by Triangle Pharmaceuticals; BMS-2322623, an azapeptide under development by Bristol-Myers Squibb as a 2nd-generation HIV-1 PI; ABT-378 under development by Abbott; and AG-1549 an imidazole carbamate under development by Agouron Pharmaceuticals, Inc.

Pentafuside (FUZEON®) a 36-amino acid synthetic peptide that inhibits fusion of HIV-1 to target membranes. Pentafuside (3-100 mg/day) is given as a continuous sc infusion or injection together with efavirenz and 2 PI's to HIV-1 positive patients refractory to a triple combination therapy; use of 100 mg/day is preferred. FUZEON binds to GP41 on the viral coating and prevents the creation of an entry pore for the capsid of the virus keeping it out of the cell.

HIV-1 infects cells of the monocyte-macrophage lineage and helper T-cell lymphocytes by exploiting a high affinity interaction of the viral enveloped glycoprotein (Env) with the CD-4 antigen. The CD-4 antigen was found to be a necessary, but not sufficient requirement for cell entry and at least one other surface protein was required to infect the cells (E. A. Berger et al., *Ann. Rev. Immunol.* 1999 17:657-700). Two chemokine receptors, either the CCR5 or the CXCR4 receptor were subsequently found to be co-receptors along with CD4 which are required for infection of cells by the human immunodeficiency virus (HIV). Antagonists of CCR5 binding have been sought to prevent viral fusion. Maraviroc (Pfizer) is a CCR5 antagonists has recently been approved by the FDA. Vicriviroc (Schering) by Pfizer is in late development stage. Numerous other companies have research programs in various discovery and development stages (see, e.g. A. Palani and J. R. Tagat, *J. Med. Chem.* 2006 49(10):2851-2857, P. Biswas et al. *Expert. Opin. Investig. Drugs* 2006 15(5):451-464; W. Kazmierski et al. *Biorg Med. Chem.* 2003 11:2663-76). CCR5 antagonists which reaching the marketplace will likely be useful in combination with NNRTIs, NRTIs and PIs.

Other antiviral agents include hydroxyurea, ribavirin, IL-2, IL-12, pentafuside. Hydroxyurea (Droxia), a ribonucleoside triphosphate reductase inhibitor shown to have a synergistic effect on the activity of didanosine and has been studied with stavudine. IL-2 (aldesleukin; PROLEUKIN®) is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314. Ribavirin, 1-β-D-ribofuranosyl-1H-1,2,4-triazole-3-carboxamide.

Commonly used abbreviations include: acetyl (Ac), atmospheres (Atm), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N, N-dimethylaminopyridine (DMAP), N,N-dimethylformamide (DMF), dimethyl sulfoxide (DMSO), 1-(3-dimethylaminopropyl)-3-ethylcarbodiimide hydrochloride (EDCI), equivalents (eq. or equiv.), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N, N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), methanol (MeOH), melting point (mp), $MeSO_2$-(mesyl or Ms), methyl (Me), acetonitrile (MeCN), m-chloroperbenzoic acid (MCPBA), mass spectrum (ms), methyl t-butyl ether (MTBE), N-methylmorpholine (NMM), N-methylpyrrolidone (NMP), phenyl (Ph), propyl (Pr), iso-propyl (i-Pr), pounds per square inch (psi), pyridine (pyr), room temperature (rt or RT), tert-butyldimethylsilyl or t-$BuMe_2Si$ (TBDMS), triethylamine (TEA or $Et_3N$), triflate or $CF_3SO_2$-(Tf), trifluoroacetic acid (TFA), O-benzotriazol-1-yl-N,N,N',N'-tetramethyluronium tetrafluoroborate (TBTU), thin layer chromatography (TLC), tetrahydrofuran (THF), trimethylsilyl or $Me_3Si$ (TMS), p-toluenesulfonic acid monohydrate (TsOH or pTsOH), 4-Me-$C_6H_4SO_2$— or tosyl (Ts), N-urethane-N-carboxyanhydride (UNCA). Conventional nomenclature including the prefixes normal (n-), iso (i-), secondary (sec-), tertiary (tert-) and neo have their customary meaning when used with an alkyl moiety. (J. Rigaudy and D. P. Klesney, Nomenclature in Organic Chemistry, IUPAC 1979 Pergamon Press, Oxford.).

TABLE I
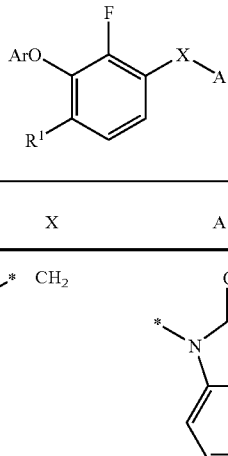
| | Ar | X | A | R¹ | MS | MP | HIV-1 RT IC₅₀ (μM) |
|---|---|---|---|---|---|---|---|
| I-1 | 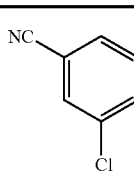 | CH₂ | 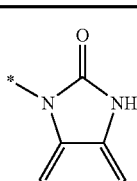 | Br | | 227.0-229.0 | 0.0122 |
| I-2 | 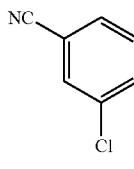 | CH₂ | 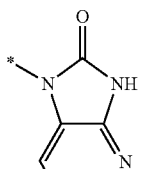 | Br | | 255.5-258.5 | 0.0058 |
| I-3 | 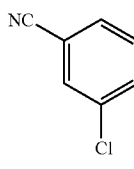 | CH₂ | 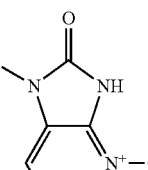 | Br | | 259.0-260.0 | 0.0159 |
| I-4 | 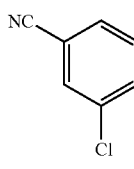 | CH₂ | 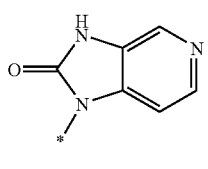 | Br | | 219.0-221.5 | 0.005 |
| I-5 | 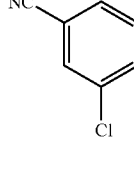 | CH₂ | 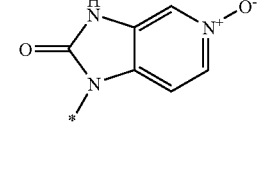 | Br | | 226.8-229 | 0.492 |
| I-6 | 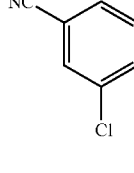 | CH₂ | 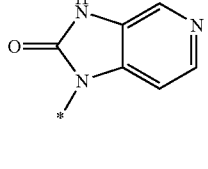 | Cl | | 232.0-233 | 0.007 |
| I-7 | 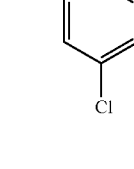 | CH₂ | 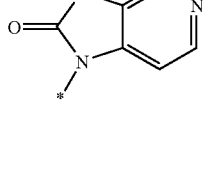 | Br | | | 0.0051 |

TABLE I-continued

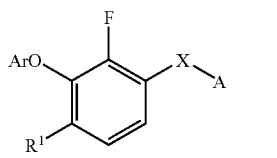

| | Ar | X | A | R¹ | MS | MP | HIV-1 RT IC$_{50}$ (μM) |
|---|---|---|---|---|---|---|---|
| I-8 | 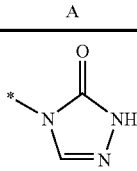 | CH$_2$ | 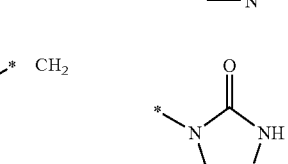 | Br | | 107 | 0.0451 |
| I-9 | 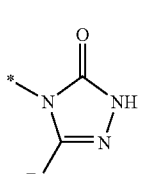 | CH$_2$ | 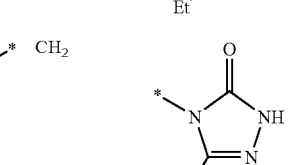 | Br | | 264.0-265.0 | 0.0197 |
| I-10 | 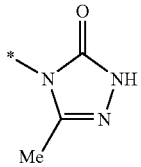 | CH$_2$ | 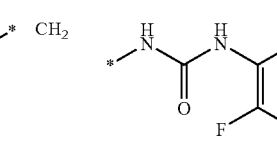 | Br | | 129.9-131.0 | 0.0546 |
| I-11 | 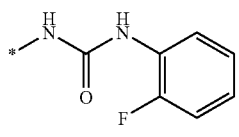 | CH$_2$ | 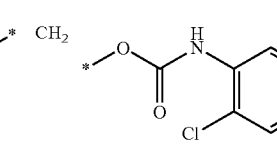 | Br | | 215.5-215.8 | 0.0331 |
| I-12 | 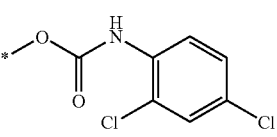 | CH$_2$ | | Br | | 138.3-139.9 | 0.0682 |

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, 2$^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 140. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted with generalized substituents; however, one skilled in the art will immediately appreciate that the nature and number of the R groups can varied to afford the various compounds contemplated in this invention. The general formulae in the schemes are intended to be illustrative and are not intended to imply a limitation to the scope of the invention which is defined by the appended claims. Moreover, the reaction conditions are exemplary and alternative conditions are well known. The reaction sequences in the following examples are not meant to limit the scope of the invention as set forth in the claims.

plifies the preparation of a compound with a 3-chloro-5-cyano-phenoxy moiety, one skilled in the art will appreciate that other phenols can be introduced analogously. For example. compounds within the scope of the invention can be prepared from 5-hydroxy-iso-phthalonitrile [CASRN 79370-78-8], 3-cyano-5-difluoromethyl-benzonitrile [CASRN 874974-85-3], 3-bromo-5-hydroxy-benzonitrile [CASRN 770718-92-8] and 3-hydroxy-5-methyl-benzonitrile [CASRN 95658-81-4].

2,4-Dihydro-[1,2,4]triazol-3-one derivatives (I-8 to I-10) were prepared analogously by alkylation A-2d with 2,4-dihydro-[1,2,4]triazol-3-one or an 5-alkyl-2,4-dihydro-[1,2,4]triazol-3-one. 5-Alkyl-2,4-dihydro-[1,2,4]triazol-3-ones were prepared by cyclization of semicarbazide with a carboxylic acid derivative (e.g. a trialkyl orthoacetate) or cyclization of a thioacylcarbamate with hydrazine.

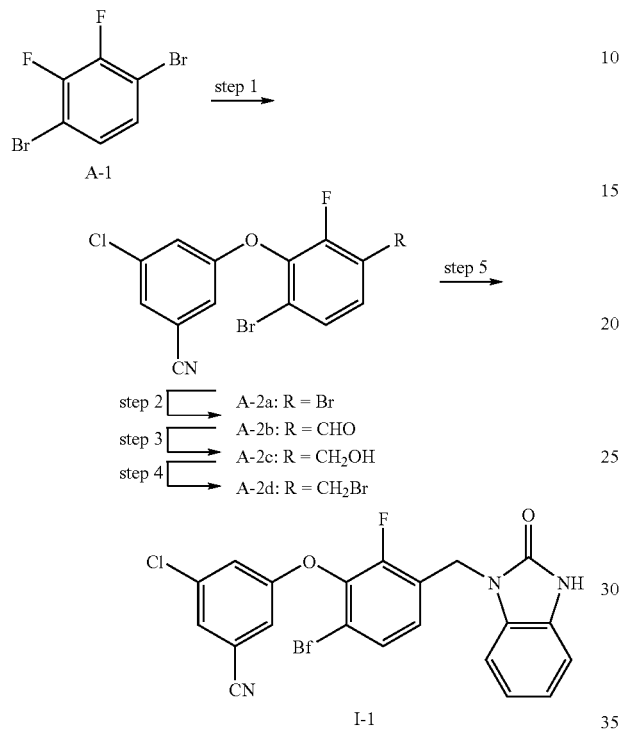

Introduction of the bis-aryl ether (step 1) can be accomplished by displacement of one of the symmetrically disposed fluorine atoms with an phenoxide salt. Fluoronitroaromatic compounds are known to be unusually sensitive to nucleophilic attack by soft nucleophiles. Fluorine substituents are generally significantly more labile than other halogen substituents. While hard nucleophiles like water and hydroxide fail to displace fluoride, soft nucleophiles like phenols, imidazoles, amines, thiols and some amides facilely displace fluorine at room temperature. (D. Boger et al., *Biorg. Med. Chem. Lett.* 2000 10: 1471-75; F. Terrier *Nucleophilic Aromatic Displacement: The Influence of the Nitro Group* VCH Publishers, New York, N.Y. 1991)

Monometallation of A-2a with iso-PrMgCl/LiCl/THF and formylation of the resulting magnesium salt with DMF afforded A-2d. Reduction of the resulting aldehyde can be achieved by utilizing well-established reagents which allow the selective reduction of the aldehyde. Sodium borohydride is known to reduce aldehydes and ketones selectively in the presence of cyano substituent. Sodium borohydride reductions are typically carried out in alcoholic or aqueous media. The conversion of a benzyl alcohol (A-2c) to a benzyl halide (A-2d) is a well-known in the art and can be carried out with a variety reagents. Commonly used reagents include $SOBr_2$, $PBr_3$, $POBr_3$ and phosphorus derived halogenating agents such as $(RO)_3PRBr$ and $R_3PBr_2$ are examples of commonly used reagents. In the present instance, phosphorus tribromide was utilized as the brominating agent (A. R. Katritzky et al. *Chem Scr.* 1987 27:477). Alkylation of A-2d with 2-hydroxy-benzimidazole directly affords I-1. While SCHEME A exem-

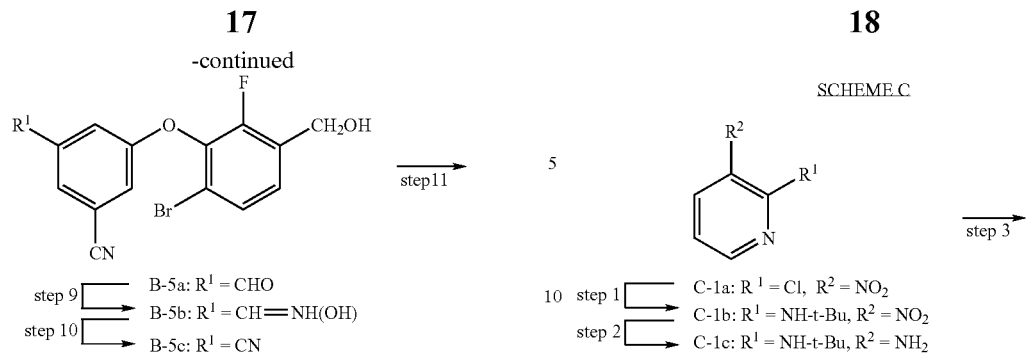

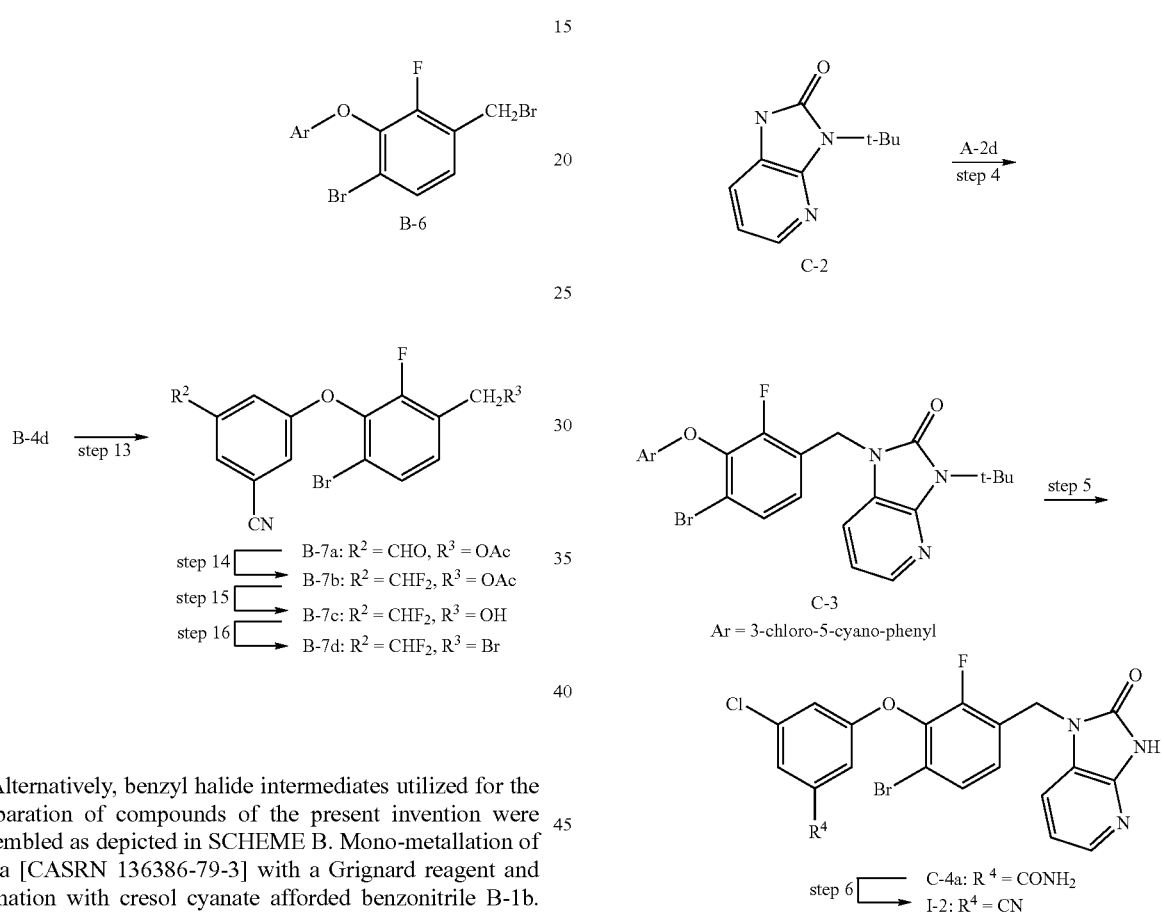

Alternatively, benzyl halide intermediates utilized for the preparation of compounds of the present invention were assembled as depicted in SCHEME B. Mono-metallation of B-1a [CASRN 136386-79-3] with a Grignard reagent and cyanation with cresol cyanate afforded benzonitrile B-1b. Metallation of B-1b and quenching the resulting organometallic with DMF afforded B-2 which was converted to B-3a with ethylene glycol and 1,2-diacetoxyethane and desilylated to afford B-3b. Condensation of B-3b and A-1, monometallation and formylation of the resulting diaryl ether, reduction of the newly introduced aldehyde to benzyl alcohol B-4c. Hydrolysis of the acetal affords B-5a which is then converted to the corresponding oxime and dehydrated to produce the 3,5-dicyanophenoxy compound B-5c. Conversion of the benzyl alcohol to the corresponding bromide B-6 is carried out as depicted in SCHEME A.

Intermediate B-4c can be used to prepare the difluoromethyl substituted intermediate. Acetylation of B-4c and selective hydrolysis of the acetal affords the aldehyde B-7a suitably protected for the introduction of the two fluorine atoms. Treatment of B-7a with DAST affords the desired difluoromethyl moiety after which hydrolysis of the acetate and introduction of the bromide affords B-7d.

1,3-Dihydro-3-tert-butyl-1,3-dihydro-imidazo[4, 5-b]pyridin-2-one (I-2) was prepared by displacement of the labile chloro substituent from C-1a with tert-butyl amine to afford C-1b. Catalytic hydrogenation of the nitro group afforded diamine C-1c which was contacted with CDI resulting in the formation of the fused imidazolidin-2-one ring. Alkylation of A-2a with C-2 was carried out analogously to the sequence depicted in SCHEME A. Removal the tert-butyl protecting was accomplished by exposure of C-3 to TTFA and MsOH which resulted in cleavage of the tert-butyl group and concomitant partial hydrolysis of the cyano substituent to the corresponding carboxamide C-4a which is treated with pyridine and TFAA to re-form the cyano substitutent.

The 1,3-dihydro-imidazo[4,5-c]pyridin-2-one and 5,7-dihydro-imidazo[4,5-c]pyridazin-6-one rings were prepared as depicted in SCHEME D.

SCHEME D

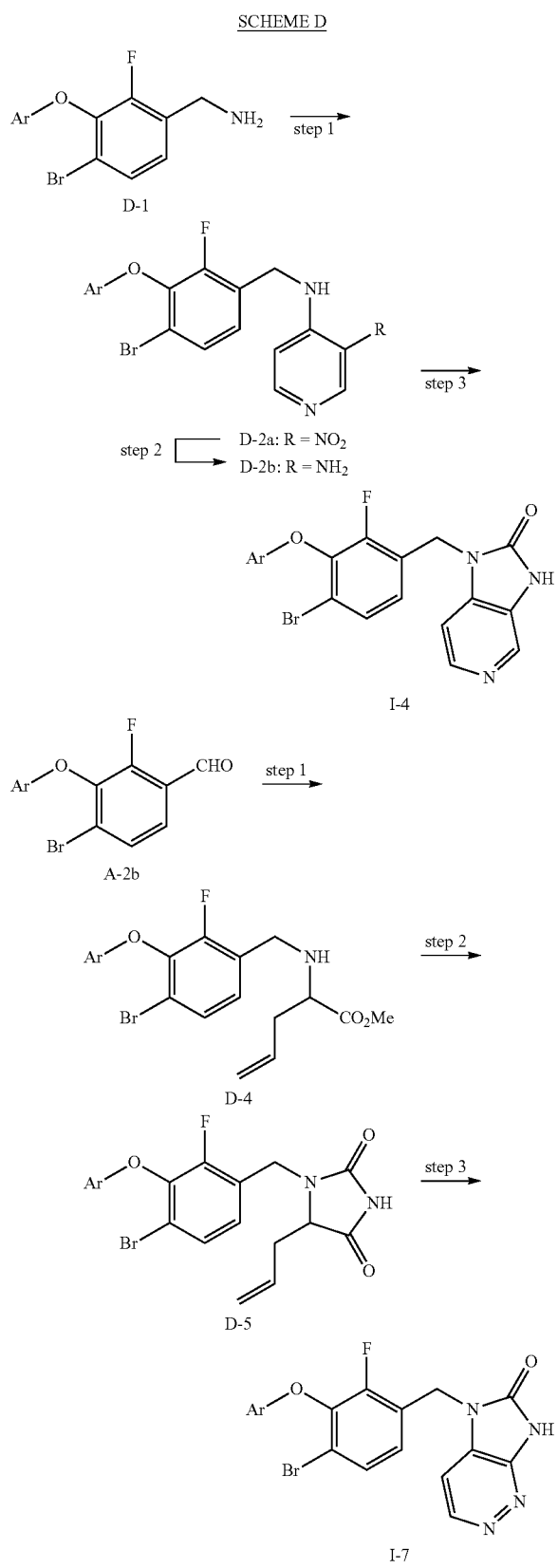

Ar = 3-chloro-5-cyano-phenyl 3-(3-Aminomethyl-6-bromo-2-fluoro-phenoxy)-5-chloro-benzonitrile (D-1) was prepared by alkylation of A-2d with the potassium salt of isoindole-1,3-dione and subsequent liberation of the amine from the phthalimide with hydrazine.

The 1,3-dihydro-imidazo[4,5-c]pyridin-2-one ring was elaborated by displacement of chloride from 4-chloro-3-nitro-pyridine with D-1 to afford D-2a. Reduction of the nitro group affords D-2b which can be directly cyclized with CDI to afford I-4. In contrast, the 5,7-dihydro-imidazo[4,5-c]pyridazin-6-one moiety was prepared by initial construction of the 5-allyl-1-methyl-imidazolidine-2,4-dione. Reductive alkylation of A-2b with methyl 2-amino-pent-4-enoate and subsequently cyclizing the alpha amino ester with trimethylsilylisocyanate yielded D-5. Osmium tetroxide mediated cleavage of the olefin afforded an aldehyde which cyclized when exposed to hydrazine to afford the 5,7-dihydro-imidazo[4,5-c] pyridazin-6-one moiety.

Reductive amination of A-2b to afford D-4 is preferably carried out carried out by combining an amine and A-2b in the presence of a complex metal hydride such as sodium borohydride, lithium borohydride, sodium cyanoborohydride, zinc borohydride, sodium triacetoxyborohydride or borane/pyridine conveniently at a pH of 1-7 optionally in the presence of a dehydrating agent such as molecular sieve or Ti(IV) (O-i-Pr)$_4$ to facilitate formation of the intermediate imine. Reductive amination procedures have been reviewed: R. M. Hutchings and M. K. Hutchings *Reduction of C=N to CHNH by Metal Hydrides in Comprehensive Organic Synthesis* col. 8, I. Fleming (Ed) Pergamon, Oxford 1991 pp. 47-54.

Compounds of the present invention wherein R$^1$ is an alkyl can be prepared from the corresponding bromide or triflate by Pd catalyzed coupling of a dialkyl zinc species. The Negishi coupling of organozinc halides or dialkylzinc with haloarenes and aryl triflates is an effective means for attachment of an alkyl group to an arene (E.-I. Negishi, *Acc. Chem. Res.* 1982 15:340-348). The reaction is catalyzed by palladium Pd(0) and palladium is preferably ligated to a bidentate ligand including Pd(dppf)Cl$_2$ and Pd(dppe)Cl$_2$. (J. M. Herbert *Tetrahedron Lett.* 2004 45:817-819) Typically the reaction is run in an inert aprotic solvent and common ethereal solvents include dioxane, DME and THF are suitable. The reaction is commonly run at elevated temperature.

Compounds of the present invention wherein R$^1$ is cyclopropyl can be prepared by Pd-mediated displacement of the bromide with tributylvinyltin (the Stille reaction) to produce the compound wherein R$^1$ is vinyl and subjecting the vinyl derivative to Pd-mediated cyclopropanation with diazomethane.

SCHEME E

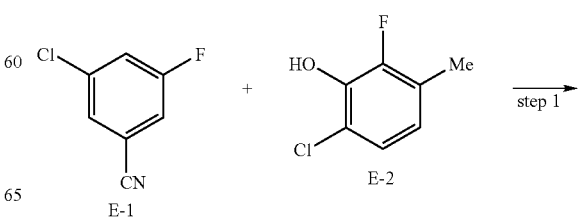

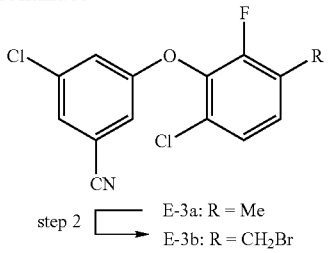

step 2 ⌈ E-3a: R = Me
       ⌊ E-3b: R = CH₂Br

Embodiments of the present invention according to formula I wherein $R^1$ is chloride can be prepared from E-3b which is prepared by condensation of E-2 (CASRN 261762-91-8) and an appropriately substituted aryl fluoride. While the reaction in SCHEME E is depicted with E-1 (CASRN 327056-73-05), other suitable aryl fluorides including 5-fluoro-isophthalonitrile (CASRN 453565-554) and 3-difluoromethyl-5-fluoro-benzonitrile (CASRN 327056-73-5) are available and can be substituted for E-1 to prepare other bis-aryl ethers analogous to E-3 useful for preparation of compounds of the present invention. Free radical bromination of the methyl substituent of E-3 with NBS and AIBN affords E-3b which is converted to compounds of the present invention were prepared as described above.

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice. "Pharmaceutically acceptable" means that which is useful in preparing a pharmaceutical composition that is generally safe, non-toxic, and neither biologically nor otherwise undesirable and includes that which is acceptable for human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent, such as a nucleoside reverse transcriptase inhibitor, another non-nucleoside reverse transcriptase inhibitor or HIV-1 protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions, and that the treatment of animals includes the treatment of humans as well as other animals. Furthermore, treatment of a HIV-1 infection, as used herein, also includes treatment or prophylaxis of a disease or a condition associated with or mediated by HIV-1 infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

Example 1

3-[6-Bromo-2-fluoro-3-(2-oxo-2,3-dihydro-benzoimidazol-1-ylmethyl)-phenoxy]-5-chloro-benzonitrile (I-1, SCHEME A)

step 1—To a solution 3-chloro-5-hydroxy-benzonitrile (153 mg, 1 mmol) and DMA (1 mL) was added NaH (42 mg, 1.05 equiv., 60% mineral oil dispersion) and the resulting mixture was stirred at 50° C. for 30 min. To the solution was added A-1 (2.7 g, 10 mmol) and the resulting mixture was heated at 125° C. for 2 h. The solution was cooled and diluted with EtOAc and the resulting solution washed with an equal volume of 10% $H_2SO_4$. The organic extract was dried ($MgSO_4$), filtered and concentrated in vacuo. The crude product was purified by $SiO_2$ chromatography eluting with 10% EtOAc/hexane to afford 331 mg (82%) of A-2a.

step 2—To a solution of A-2a (2.00 g, 4.93 mL) in PhMe (40 mL) maintained under an Ar atmosphere and cooled to −78° C. was added a solution of i-PrMgCl (2M in THF, 3.08 mL, 6.16 mmol). The solution was stirred for 1 h then a solution of CuCN.2LiCl (1 M in THF, 0.1 mL) was added. The resulting solution was stirred at −50° C. for 2 h and then the reaction mixture was cannulated into a flask containing DMF (0.57 mL, 7.4 mmol) and PhMe (10 mL) which was maintained at −78° C. The mixture was warmed to RT and quenched by the addition of saturated aqueous NH4Cl solution. The organic phase was separated, washed with brine, dried (MgSO4) and evaporated to dryness in vacuo to afford 1.50 g (86%) of A-2b as an off-white solid.

step 3—Sodium borohydride was added in portions to a stirred solution of A-2b in THF (5 mL) and MeOH (5 mL) at RT. After stirring for 24 h, the reaction mixture was quenched by the addition of saturated aqueous NH4Cl. The organics were extracted with EtOAc, washed with brine, dried (MgSO4) and evaporated to dryness in vacuo. The product was purified by SiO2 chromatography eluting with an EtOAc/hexane gradient (10 to 50% EtOAc) to afford 0.25 g (31%) of A-2c.

step 4—To a stirred solution of A-2c (3.00 g, 8.41 mmol) in DCM (100 mL) was added a solution of PBr3 (9.3 mL, 1M in DCM). After stirring at RT under $N_2$ for 24 h the reaction mixture was quenched by the addition of saturated aqueous NaHCO3. The organic phase was separated, washed with brine, dried (MgSO4) and evaporated in vacuo. The product was purified by SiO2 chromatography eluting with an EtOAc/hexane gradient (20 to 50% EtOAc) to afford 2.0 g (57%) of A-2d as white crystals.

step 5—A mixture of A-2d (0.448 g, 1.07 mmol), 2-hydroxybenzimidazole (CASRN 615-16-7, 0.860 g, 6.41 mmol), $K_2CO_3$ (0.295 g, 2.13 mmol) and DMF (2 mL) was heated in a microwave at 100° C. for 10 min. The reaction mixture was cooled, diluted with EtOAc, washed with brine, dried ($Na_2SO_4$) and evaporated to dryness. The residue was triturated with EtOAc to remove the excess 2-hydroxybenzimidazole. The filtrate was evaporated to afford 0.180 g (35%) of I-1 as an off-white solid: mp 227-229° C.; Found: C, 53.15; H, 2.53; N, 8.79. $C_{21}H_{12}BrClFN_3O_2$ requires C, 53.36; H, 2.56; N, 8.89.

Example 2

3-[6-Bromo-2-fluoro-3-(2-oxo-2,3-dihydro-imidazo [4,5-c]pyridin-1-ylmethyl)-phenoxy]-5-chloro-benzonitrile (I-4, SCHEME D)

3-(3-Aminomethyl-6-bromo-2-fluoro-phenoxy)-5-chloro-benzonitrile

The potassium salt of isoindole-1,3-dione (10.5 g, 1.1 equiv) was added to a solution of the A-2d (21.6 g, 52 mmol) in DMF (200 mL), and the solution was stirred at 50 C for 16 h. Solid precipitated out of solution after a short period. The reaction was cooled to RT, poured into 300 mL of water, and filtered. The solid was washed with a small amount of $Et_2O$, dried in the filter funnel under vacuum to afford 20 g (80%) 3-[6-bromo-3-(1,3-dioxo-1,3-dihydro-isoindol-2-ylmethyl)-2-fluoro-phenoxy]-5-chloro-benzonitrile.

Hydrazine (1.62 mL, 5 equiv) was added slowly to a suspension of the imide (5.0 g, 10 mmol) in a mixture of THF (80 mL) and EtOH (20 mL). The solution was slowly heated to 80° C. and the reaction mixture became homogenous. After 1 h, most of the solvent was removed in vacuo, and the residue was partitioned between EtOAc/hexanes and water. The organic layer was washed with aqueous NaHCO3, and the organic layer was evaporated. The crude product was purified by SiO2 chromatography eluting with a DCM/60:10:1 DCM: MeOH:NH4OH gradient (0 to 30% of the DCM/MeOH/NH4OH solution) to afford 1.25 g (34%) of 3-(3-aminomethyl-6-bromo-2-fluoro-phenoxy)-5-chloro-benzonitrile.

step 1—4-chloro-3-nitro-pyridine (180 mg, 1.2 equiv) and Na2CO3 (188 mg, 2.3 equiv) were added to a solution of D-1 (275 mg, 0.77 mmol) in DMA (5 mL). After stirring for 2.5 h at 50° C. the entire reaction mixture was poured into water (20 mL) and extracted EtOAc. The organic layers were washed with brine, dried (MgSO4), concentrated in vacuo. The crude product was purified by SiO2 chromatography eluting with a EtOAc/hexane gradient (33 to 65% EtOAc) to afford 0.280 g (76%) of D-2a.

step 2—Ammonium chloride (124 mg, 4.0 equiv), H2O (1 mL), and Fe powder (130 mg, 4.0 equiv) were slowly added to a solution of nitro compound D-2a (277 mg, 0.58 mmol) in EtOH (3 mL). After heating for 2.5 h at 100° C. the reaction mixture was cooled to RT, filtered through CELITE® and concentrated in vacuo. The crude product was purified by SiO2 chromatography eluting with a MeOH/DCM gradient (5 to 15% MeOH) to afford 0.085 g (33%) of D-2b.

step 3—CDI (34 mg, 1.1 equiv) was added to a solution of D-2b (85 mg, 0.19 mmol) in DMF (1 mL). After stirring for 3 d at 50° C., an additional portion of CDI was added and the temperature increased to 100° C. After 4 h, the reaction mixture was cooled, poured into H2O (5 mL), and extracted EtOAc. The organic layers were then washed with brine, dried (MgSO$_4$), filtered and concentrated in vacuo. Trituration of the residue with Et$_2$O afforded 0.060 g (66%) of I-4.

Example 3

3-[6-Bromo-2-fluoro-3-(2-oxo-2,3-dihydro-imidazo[4,5-b]pyridin-1-ylmethyl)-phenoxy]-5-chloro-benzonitrile (I-2, SCHEME C)

steps 1 & 2—tert-Butylamine (19 mL, 3 equiv) was added to a solution of C-1a (9.5 g, 59.9 mmol) and DMF (150 mL). After stirring for 2 d at 45° C. the reaction mixture was concentrated in vacuo. After redissolving the residue in Et$_2$O (300 mL) the organic layer was washed water then brine, dried (MgSO$_4$), filtered and concentrated in vacuo to afford C-1b which was used without further purification. To a solution of C-1b and MeOH (50 mL) was added 10% Pd/C (1 g). The resulting suspension was stirred under a H$_2$ atmosphere for 18 h, filtered through CELITE® and concentrated in vacuo. The crude product was purified by SiO$_2$ chromatography eluting with an EtOAc/hexane gradient (10 to 50% EtOAc) to afford 3.3 g (33%) of C-1c and 6.1 g recovered C-1b.

step 3—CDI (4.5 g, 1.3 equiv) was added to a solution of C-1c (3.3 g, 21.1 mmol) in MeCN (50 mL) and the reaction mixture was stirred for 2 h at 50° C. After the reaction was complete the mixture was concentrated in vacuo, re-dissolved in EtOAc (300 mL), washed with water and brine, dried (MgSO$_4$), filtered and concentrated in vacuo. The crude product was purified by SiO$_2$ chromatography eluting with an EtOAc/hexane gradient (10 to 50% EtOAc) to afford 2.6 g (64%) of C-2.

step 4—To a solution of C-2 (100 mg, 1.1 equiv) in DMF (2 mL) at 0° C. was added NaH (24 mg, 1.25 equiv, 60% mineral oil dispersion). After stirring for 15 min, A-2d (199 mg, 0.475 mmol) was added, and stirring was continued at RT for 30 min at which point the entire reaction mixture was poured into H$_2$O (10 mL) and extracted EtOAc. The organic layers were then washed with brine, dried (MgSO$_4$), filtered and concentrated in vacuo. The crude product was purified by SiO$_2$ chromatography eluting with an EtOAc/hexane gradient (10 to 30% EtOAc) to afford 0.200 g (72%) of C-3.

steps 5 & 6—A solution of C-3 (175 mg, 0.33 mmol), TFA (1.3 mL) and MsOH (0.33 mL) was heated to 75° C. for 4 h. Upon completion, the reaction mixture was concentrated in vacuo, redissolved in EtOAc (300 mL), washed sequentially with H$_2$O and brine, dried (MgSO$_4$), filtered and concentrated in vacuo. The crude product which was found to be the amide C-4a (135 mg, 0.275 mmol). This material was suspended in dioxane (1.4 mL) and successively treated with pyridine (200 µL, 9 equiv) and TFAA (112 µL, 3 equiv) at 0° C. The mixture was then gently warmed to 60° C. for 5 h. The mixture was poured into 20 mL of water, and extracted EtOAc. The organic layers were washed with brine, dried (MgSO$_4$), concentrated in vacuo and triturated with Et$_2$O to afford I-2.

Example 4

3-[6-Bromo-2-fluoro-3-(6-oxo-6,7-dihydro-imidazo[4,5-c]pyridazin-5-ylmethyl)-phenoxy]-5-chloro-benzonitrile (I-7; SCHEME D)

step 1—Allylglycine methyl ester (730 mg, 1.0 equiv, free base liberated from the HCl salt in Et$_2$O with sat. Na$_2$CO$_3$) was dissolved in DCE (25 mL). To this solution was added A-2b (2 g, 5.6 mmol) followed by NaBH(OAc)$_3$ (1.66 g, 1.4 equiv). After stirring overnight the reaction mixture was quenched with sat'd. Na$_2$CO$_3$ and extracted with Et$_2$O. The organic layers were washed with brine, dried (MgSO$_4$), filtered and concentrated in vacuo. The crude product was purified by SiO$_2$ chromatography eluting with an EtOAc/hexane gradient (20 to 30% EtOAc) to afford 1.25 g (48%) of D-4.

step 2—Trimethylsilylisocyanate (1 mL, 2.5 equiv) and DMAP (32 mg, 0.10 equiv) were added to a solution of D-4 (1.20 g, 2.60 mmol) in THF (13 mL). This solution was heated at 50° C. for 3 d, cooled and concentrated in vacuo. The crude product was purified by SiO$_2$ chromatography eluting with an EtOAc/hexane gradient (33 to 66% EtOAc) to afford 1.11 g (88%) of the hydantoin D-5.

step 3—To a solution of D-5 (1.02 g, 2.13 mmol) in THF (8.5 mL) was added OsO$_4$ (100 µL, 5% in tert-BuOH) followed by a solution of NaIO$_4$ (1.36 g, 3 equiv) in H$_2$O (2.8 mL). After stirring for 24 h, the thick mixture was diluted with sat. NaHCO$_3$, and extracted with EtOAc. The organic layers were then washed with brine, dried (MgSO$_4$), filtered and concentrated in vacuo to give a yield the corresponding aldehyde. The crude aldehyde was dissolved in AcOH (17 mL) and hydrazine (670 µL, 10 equiv.) was added. After heating for an additional 24 h, the mixture was concentrated in vacuo and purified by SiO$_2$ chromatography eluting with a MeOH/DCM gradient (1 to 7% MeOH) to afford a slightly impure product that was further purified by HPLC to afford I-7.

Example 5

3-[6-Bromo-2-fluoro-3-(5-oxo-1,5-dihydro-[1,2,4]triazol-4-ylmethyl)-phenoxy]-5-chloro-benzonitrile (I-8)

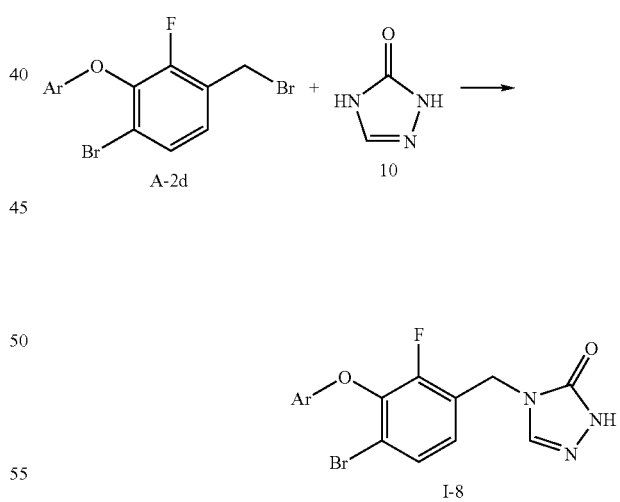

Ar=3-chloro-5-cyano-phenyl

A solution of A-2d (200 mg, 0.477 mmol), 2,4-dihydro-[1,2,4]triazol-3-one (10, CASRN 930-33-6, 0.040 g, 1.0 eq), K$_2$CO$_3$ (0.13 g, 2.0 eq), and KI (0.008 g, 0.1 eq) and MeCN (1.5 mL) was heated to 85° C. for 2 h and then cooled to RT. The reaction mixture was diluted with 10% MeOH/DCM, and washed sequentially with water and brine. The organic extracts were evaporated and the crude product purified by SiO$_2$ chromatography eluting with a MeOH/DCM gradient (3-10% MeOH) to afford 0.020 g (10%) of 1-8 as a white solid.

Example 6

3-[6-Bromo-3-(3-ethyl-5-oxo-1,5-dihydro-[1,2,4]triazol-4-ylmethyl)-2-fluoro-phenoxy]-5-chloro-benzonitrile (I-9)

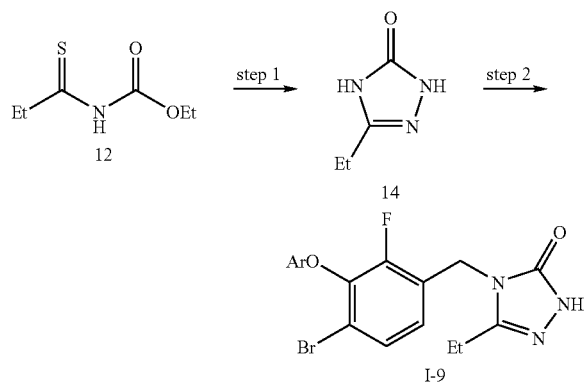

Ar=3-chloro-5-cyano-phenyl step 1—To a solution of ethyl (thiopropionyl)carbamate (12, CASRN 72139-54-9, 0.28 g, 1.74 mmol) and EtOH (3 mL) at RT was added hydrazine (0.1 mL, 2 eq) and the resulting solution heated at 80° C. for 2 h. The reaction mixture was cooled, and concentrated in vacuo. The solid was washed with EtOAc to afford 0.15 g (76%) of 14.

step 2—A solution of A-2d (0.15 g, 0.358 mmol), 14 (0.04 g, 1.0 eq), K$_2$CO$_3$ (0.1 g, 2 eq), and KI (0.004 g, 0.1 eq) and MeCN (2.5 mL) was heated at 75° C. for 24 h. The reaction mixture was diluted with 10% MeOH/DCM and the organic layer washed sequentially with H$_2$O and brine. The combined organic extracts were dried (Na$_2$SO$_4$), filtered and concentrated in vacuo. The crude product was purified by SiO$_2$ chromatography eluting with a MeOH/DCM gradient (1-7% MeOH) to afford 0.015 g (9%) of I-9.

Example 7

3-[6-Bromo-2-fluoro-3-(3-methyl-5-oxo-1,5-dihydro-[1,2,4]triazol4-ylmethyl)-phenoxy]-5-chloro-benzonitrile (I-10)

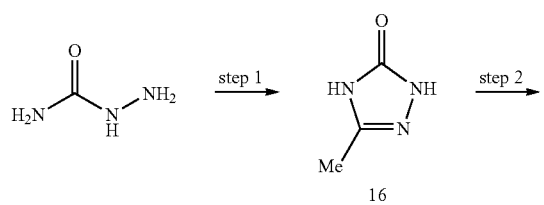

step 1—A solution of semicarbazide (1 g, 9 mmol), trimethylorthoacetate (2.5 mL, 2.2 eq) and MeOH (10 mL) was stirred at RT for 18 h. The volatile material was removed in vacuo and the solid washed with toluene and filtered to afford 0.8 g (79%) of 16.

step 2—A solution of A-2d (0.12 g, 0.286 mmol), 16 (0.035 g, 1.25 eq), K$_2$CO$_3$ (0.1 g, 2.5 eq), and KI (0.005 g, 0.1 eq), acetone (1 mL) and MeCN (2.5 mL) was heated at 45° C. for 24 h. The reaction mixture was diluted with 10% MeOH/DCM and the organic layer washed sequentially with H$_2$O and brine. The combined organic extracts were dried (Na$_2$SO$_4$), filtered and concentrated in vacuo. The crude product purified by SiO$_2$ chromatography eluting with a MeOH/DCM gradient (1.5-7% MeOH) to afford 0.020 g (16%) of I-10.

Example 8

3-Chloro-5-[6-chloro-2-fluoro-3-(2-oxo-2,3-dihydro-imidazo[4,5-c]pyridin-1-ylmethyl)-phenoxy]-benzonitrile (I-6, SCHEME E)

step 1—To a solution of 3-chloro-5-fluorobenzonitrile (E-1, 10 g, 64.28 mmol) and 6-chloro-2-fluoro-3-methyl-phenol (E-2, 9.38 g, 58.44 mmol) in DMA (100 mL) was added Cs$_2$CO$_3$ (1.9 g, 5.84 mmol) followed by K$_2$CO$_3$ (8.9 g, 64.28 mmol). The mixture was heated to 120° C. (oil bath) under argon for 5.5 h. The reaction was cooled to RT and water (150 mL) was added. The mixture was extracted with EtOAc (150 mL) and the aqueous phase back extracted with EtOAc (2×100 mL). The combined EtOAc extracts were dried (MgSO$_4$), filtered and concentrated in vacuo afford 11.1 g (75% purity) of E-3a as a white crystalline solid.

step 2—To a solution of E-3a (11.1 g, 75% pure, 28 mmol) in CCl$_4$ (100 mL) was added NBS (5.4 g, 30 mmol) followed by AIBN (450 mg, 2.74 mmol). The mixture was heated to just below reflux temperature for 5 h. Additional NBS (2.7 g) and AIBN (200 mg) were added and heating continued for an additional 5 h. The material was cooled to RT and filtered to remove precipitated succinimide. The filtrate was concentrated and the remainder taken up in EtOAc (100 mL) and shaken with brine (100 mL). The EtOAc phase was collected and the aqueous phase back extracted with EtOAc (2×80 mL). The combined organic extracts were dried (MgSO$_4$), filtered and concentrated in vacuo. The product was purified by SiO$_2$ chromatography eluting with an EtOAc/hexane gradient (1.5-8% EtOAc) to afford 6.8 g (65%) of E-3b as a white crystalline solid.

I-6 was prepared from E-3b by a procedure analogous to that described in Example 2 except E-3b was used in place of A-2b.

Example 10

Ureas and carbamates which are exemplified by I-11 and I-12 can be prepared by condensation of D-1 or A-2c (wherein the 3-chloro-5-cyano-phenyl moiety can be replaced by an substituted phenyl moiety within the scope of the invention) respectively with an isocyanate. A vast number of isocyanates are commercially available or alternatively, they are readily prepared from an aryl amine and phosgene.

Example 11

5-[6-Bromo-2-fluoro-3-(2-oxo-2,3-dihydro-benzoimidazol-1-ylmethyl)-phenoxy]-isophthalonitrile (SCHEME B, 20)

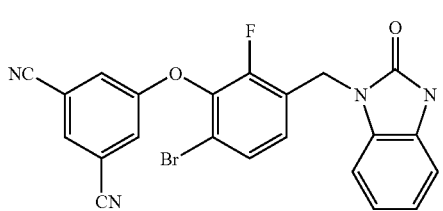

(20)

Cresol cyanate—Bromine (100 mL; 1.06 eq) was placed under $H_2O$ (350 mL) in a reactor and coolant was circulated through the jacket. An ice-water bath was used for cooling. In a separate vessel, a solution of NaCN (100 g, 1.11 equiv) in $H_2O$ (350 mL) was prepared and this was solution added to the bromine/water at a rate that maintained the temperature at ≦30° C. The resulting slurry of cyanogen bromide is added to a solution of o-cresol (209 g, 1.00 equiv.) in toluene (900 mL). The biphasic mixture is stirred vigorously and cooled below 10° C. TEA (270 mL, 0.98 equiv.) is added while maintaining the temperature at <10° C. The stirring was suspended and the aqueous phase withdrawn and replaced with heptane (540 mL). The organic phase was sequentially washed with dilute NaOH (1.20 equiv.), water, 2M HCl (0.4 equiv.) water, saturated $NaHCO_3$, and water while the temperature was maintained at ≦15° C. The heptane solution is dried by brief vacuum distillation (temperature ≦35° C.) and tested by Karl Fischer analysis. The organic phase solution was stored until further use.

step 1—A degassed reactor was charged with a THF solution of iso-PrMgCl (1.14 equiv., 2M solution in THF) and B-1a (495.2 g, 1.352 mol; CASRN 136386-79-3) was pumped into the reactor while the temperature below 65° C. with a water bath. After the exothermicity subsided, the reaction was stirred at RT until metallation was complete (Aliquots removed, quenched with dil. $H_2SO_4$ and assayed by gas chromatography). The resulting solution containing the aryl Grignard reagent was added to a heptane solution of cresol cyanate (supra; CASRN 1123-89-3) while maintaining the reaction temperature below 10° C. The reaction was monitored by removing aliquots, quenching with dilute and $H_2SO_4$ and assaying the cresol/cyanate ratio. When the cyanate was consumer the reaction mixture was added to a dilute $H_2SO_4$ solution (86.5 g $H_2SO_4$ and 2.15 L $H_2O$). The aqueous layer was separated and the remaining organic phase was diluted with heptane and washed sequentially with ice cold aqueous NaOH (320 g of 50% NaOH and 1 kg of ice), water, saturated $NH_4Cl$ and water. The solution was dried by azeotropic distillation and the product was purified by vacuum distillation to afford 395.7 g (93.7%) B-1b contaminated with 3-6% 3-(tert-butyl-dimethylsilyloxy)-bromobenzene.

steps 2-4—A reactor was charged with a solution of B-1b (36 kg) and toluene/heptane (65 kg). and the solution was cooled to less then −50° C. by direct injection of liquid $N_2$ under the surface of the solution. A solution of iso-propyl-magnesium chloride (70 kg, 2.0 M in THF) was added at a rate that the reaction temperature was maintained below −20° C. (liquid $N_2$ was added as required to maintain the desired temperature). The addition required ca. 50 min. A −20° C. cooling solution was circulated through the vessel jacket and the resulting reaction mixture was stirred at −20° C. for at least 1 h. The progress of the metallation was monitored by removing and quenching aliquots with dilute $H_2SO_4$ and assaying by HPLC. DMF (ca. 30 kg) cooled to <−10° C. and transferred at a rate that maintained the temperature below 0° C. during the transfer step. The reaction was slowly warmed to 20° C. and aliquots removed, quenched and analyzed by hplc. The reaction was recooled to 0° C. and a solution of 8.2 kg $H_2SO_4$ and 90 L of $H_2O$ was added while maintained the reaction mixture below 10° C. The reaction vessel was charged with MTBE (50 kg) an agitated for at least 15 min. The phases were separated and the aqueous phase was withdrawn from the vessel. The remaining organic solution was again washed with $H_2O$ (110 L) and the aqueous phase discarded.

The reaction vessel was fitted with a condenser cooled to 5° C. and a Dean-Stark trap which could be switched from reflux to full take-off The vessel was purged with $N_2$ and p-TsOH (0.5 kg), ethylene glycol (22 kg) and ethylene glycol diacetate (22 kg) were added sequentially. The THF and MTBE were removed by distillation (jacket temperature between 80 and 95° C.). After the distillation was complete the Dean-Stark trap was set to reflux and the jacket temperature was raised to ca. 100° C. and ethylene glycol and water removed azeotropically. Additional toluene could be added as required. Azeotropic removal of water was continued until less than 1% of the aldehyde was detected by HPLC. The reaction mixture was cooled to 25° C. and a saturated solution of $NaHCO_3$ (25 kg) and water (75 L) were added, the solutions agitated, allowed to separate and the aqueous solution withdrawn. The residual organic phase was washed with $H_2O$ (100 L). The reaction vessel was fitted for distillation and solvents were removed, initially at atmospheric pressure, then under vacuum with the jacket warmed to 60° C.

When only toluene and B-3a remained, the reaction was cooled to 25° C. and DME (70 kg) was added. The solution was cooled to between −10° C. and −20° C. and a 15% aqueous NaOH cooled to 10° C. was added over about 30 min (maintaining the reaction temp at <−10° C.). Aliquots of the reaction were removed and when desilylation was complete the reaction mixture was diluted with $H_2O$ (80 L), cooled to <0° C. and the pH of the reaction mixture was adjusted to 6-7 with cold 6.0 M $H_2SO_4$ (13.2 kg con $H_2SO_4$ and 22 L $H_2O$). The mixture was partitioned into MTBE (130 kg). The aqueous layer was withdrawn and back extracted MTBE. The combined organic extracts were washed with $H_2O$, the aqueous layer withdrawn and the volatile solvents distilled until the reaction volume was about 50-70 L. The residual organic phase was diluted with heptane (20 kg) and the resulting precipitated phenol filtered and dried in a Nutsche filter to afford B-3b.

step 5—A solution of B-3b (6.0 g, 31.38 mmol), $K_2CO_3$ (4.76 g, 34.52 mmol) and DMA (48 mL) was stirred for 5 min. To the solution was added 1,4-dibromo-2,3-difluoro-benzene (85.33 g, 0.3138 mol) and the solution was heated at 125° C. for 55 min. HPLC analysis indicated the starting material had been consumed. The reaction mixture was diluted with $H_2O$ (73 mL), stirred well then the bottom organic layer was withdrawn. The organic phase diluted with $H_2O$ (900 mL) then the excess dibromo-difluoro-benzene was removed by steam distillation. The remaining solution was extracted with DCM (50 mL) and the organic phase separated and diluted with MeOH (115 mL). The flask was fitted for distillation and solvent distilled until thermometer was steady at 65° C. for 10 min. The reaction mixture was slowly cooled to 6° C. and the resulting solid filtered and twice washed with MeOH. The while solid was dried in vacuo to afford 9.7 g of B-4a.

step 6—iso-PrMgCl (15.6 mL, 1.4 equiv) was added dropwise to a solution of B-4a (10 g, 22.6 mmol) and toluene (140 mL) cooled to −78° C. The reaction mixture was stirred at −78° C. for 4 h, warmed briefly to −20° C., and then re-cooled to −78° C. DMF (3.4 mL) was added to the reaction mixture and the reaction was warmed to RT, quenched with $NH_4Cl$, and extracted with EtOAc. The crude product was purified by $SiO_2$ chromatography eluting with 25% EtOAc/hexanes to afford 5.93 g (68%) of B-4b.

step 7—$NaBH_4$ (1.14 g, 2 equiv) was added to a solution of B-4b (5.93 g, 15.1 mmol) in a mixture of THF (25 mL) and EtOH (25 mL). The reaction was stirred at RT for 2 h, then stored at 0° C. overnight. The mixture was quenched with $H_2O$, extracted with EtOAc, dried ($MgSO_4$), and concentrated in vacuo. The crude product was purified by $SiO_2$ chromatography (45% EtOAc/hexanes) to afford 5.4 g (91%) of B-4c as a clear oil/foamy solid.

step 8—An aqueous solution of TsOH (0.14 g in 6 mL $H_2O$, 0.06 equiv) was added to a solution of B-4c (5.4 g, 13.7 mmol) in MeCN (20 mL) and $H_2O$ (20 mL). The mixture was heated to 70° C. for 2 h, then stirred at RT overnight. The mixture was extracted with EtOAc, and the combined organic extracts were washed with $NaHCO_3$, brine, dried ($MgSO_4$) and concentrated in vacuo to afford 4.1 g (87%) of B-5a.

step 9—Hydroxylamine hydrochloride (2.1 g, 1.05 equiv) was added in three portions to a solution of $NaHCO_3$ (2.55 g, 1.05 equiv) in $H_2O$ (168 mL). A solution of B-5a (10.12 g, 28.9 mmol) in THF (168 mL) was added, and the reaction was stirred at RT. When the reaction was complete (ca. 3 h), the mixture was separated, the aqueous layer was washed with $NH_4Cl$ solution, diluted HCl, and extracted with EtOAc. The combined organic layers were dried ($MgSO_4$), filtered, and concentrated in vacuo. The crude product was purified by $SiO_2$ chromatography eluting with EtOAc/hexanes to afford 8.62 g (82%) of B-5b as an oil that slowly solidified.

step 10—TFAA (6.5 mL, 2 equiv) was added to a solution of B-5b (8.62 g, 24 mmol) in a mixture of pyridine (11.5 mL, 6 equiv) and dioxane (57 mL) cooled to 0° C. The reaction mixture was heated to 65° C. for several hours, then cooled to RT and stirred overnight. The dark yellow mixture was diluted with DCM, and washed with water and diluted HCl. The organic layer was dried ($MgSO_4$), filtered and concentrated in vacuo to afford a yellow oil that was purified by $SiO_2$ chromatography eluting with 40% EtOAc/Hexanes to afford a mixture of the alcohol and the corresponding trifluoroacetate (5.91 g). This mixture was dissolved in THF, and a $H_2O$ solution of LiOH (840 mgs, ca. 1.5 equiv) was added dropwise at 0° C. The mixture was stirred at 0° C. for 1 h, quenched with 1 N HCl, and extracted with EtOAc. The combined organic layers were dried ($MgSO_4$), filtered, and concentrated to afford 4.9 g (59%) of B-5c as a white solid slightly contaminated with the starting ester.

step 11—A solution of $PBr_3$ (15 mL of a 1.0 M solution in DCM, 1.1 equiv) was added to a solution of B-5c (4.81 g, 13.9 mmol) in DCM (23 mL). The solution was stirred at RT for 2 h. The mixture was quenched with $NaHCO_3$, extracted with DCM, dried ($MgSO_4$), filtered and concentrated to afford a yellow oil. The product was purified by $SiO_2$ chromatography eluting with 20% EtOAc/hexanes to afford 1.9 g of B-6 as a white solid.

5-[6-Bromo-2-fluoro-3-(2-oxo-2,3-dihydro-benzoimidazol-1-ylmethyl)-phenoxy]-isophthalonitrile can be prepared from B-6 and 2-hydroxybenzimidazole utilizing the procedure described in step 5 of example 1.

Example 12

5-[6-Bromo-2-fluoro-3-(2-oxo-2,3-dihydro-benzoimidazol-1-ylmethyl)-phenoxy]-isophthalonitrile (22)

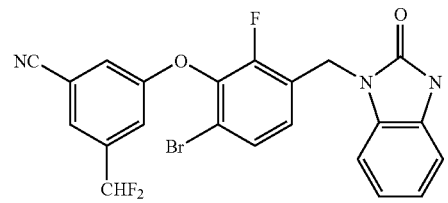

step 12—Acetic anhydride (0.93 g, 1.5 equiv) was added to a solution of the B-4c (2.4 g, 6.1 mmol) and TEA (0.93 g, 1.5 equiv) in MeCN (10 mL). The solution was stirred at RT for 1 h, diluted with EtOAc, washed with $NaHCO_3$ solution, dried ($Na_2SO_4$), filtered and concentrated to afford 2.2 g (82%) of B-4d as a clear oil.

step 2—A solution of p-TsOH (60 mg, 0.06 equiv) in $H_2O$ (6 mL) was added to a solution of the B-4d (2.2 g, 5.0 mmol) in MeCN (8 mL). The resulting solution was heated at 70° C. for 5 h. The solution was then cooled to RT, diluted with EtOAc, and washed with saturated $NaHCO_3$ solution and brine. The organic layer was dried ($Na_2SO_4$) and concentrated. The crude product was purified by $SiO_2$ chromatography eluting with EtOAc/hexane to afford 1.3 g (62%) of B-7a as a clear oil.

step 3—To a solution of the B-7a (0.12 g, 0.3 mmol) in DCM (1 mL) cooled to 0° C. was added a drop of EtOH followed by DAST (0.92 g, 1.2 equiv). The solution was warmed to RT and left at this temperature overnight. The mixture was then carefully poured onto ice. Saturated $NaHCO_3$ was added, and the mixture was extracted with DCM, dried ($Na_2SO_4$), filtered and concentrated to afford B-7b. This product was dissolved in THF (10 mL) and a of 2M LiOH (1.75 mL) in $H_2O$ was added and the mixture was stirred for 3 h. The reaction was quenched with 1N HCl, extracted with EtOAc, dried ($Na_2SO_4$), filtered and concentrated. Purification of the residue by $SiO_2$ chromatography afforded 0.074 g (67%) of B-7c.

5-[6-Bromo-2-fluoro-3-(2-oxo-2,3-dihydro-benzoimidazol-1-ylmethyl)-phenoxy]-isophthalonitrile (22) can be prepared from B-7c using procedures analogous to those described in steps 4 and 5 of example 1.

Example 13

HIV-1 Reverse Transcriptase Assay

RNA-dependent DNA polymerase activity was measured using a biotinylated primer oligonucleotide and tritiated dNTP substrate. Newly synthesized DNA was quantified by capturing the biotinylated primer molecules on streptavidin coated Scintillation Proximity Assay (SPA) beads (Amersham). The sequences of the polymerase assay substrate were: 18 nt DNA primer, 5'-Biotin/GTC CCT GTT CGG GCG CCA-3'; 47 nt RNA template, 5'-GGG UCU CUC UGG UUA GAC CAC UCU AGC AGU GGC GCC CGA ACA GGG AC-3'. The biotinylated DNA primer was obtained from the Integrated DNA Technologies Inc. and the RNA template was synthesized by Dharmacon. The DNA polymerase assay (final volume 50 µl) contained 32 nM biotinylated DNA primer, 64 nM RNA substrate, dGTP, dCTP, dTTP (each at 5 µM), 103 nM [$^3$H]-dATP (specific activity=29 µCi/mmol), in 45 mM Tris-HCl, pH 8.0, 45 mM NaCl, 2.7 mM Mg(CH$_3$COO)$_2$, 0.045% Triton X-100 w/v, 0.9 mM EDTA. The reations contained 5 ul of serial compound dilutions in 100% DMSO for IC50 determination and the final concentrations of DMSO were 10%. Reactions were initiated by the addition of 30 µl of the HIV-1 RT enzyme (final concentrations of 1-3 nM). Protein concentrations were adjusted to provide linear product formation for at least 30 min of incubation. After incubation at 30° C. for 30 min, the reaction was quenched by addition of 50 µl of 200 mM EDTA (pH 8.0) and 2 mg/ml SA-PVT SPA beads (Amersham, RPNQ0009, reconstituted in 20 mM Tris-HCl, pH 8.0, 100 mM EDTA and 1% BSA). The beads were left to settle overnight and the SPA signals were counted in a 96-well top counter-NXT (Packard). IC$_{50}$ values were obtained by sigmoidal regression analysis using GraphPad.

Example 14

Antiviral Assay Method

Anti-HIV-1 antiviral activity was assessed using an adaptation of the method of Pauwels et al. (Pauwels et al., *J Virol Methods* 1988 20:309-321). The method is based on the ability of compounds to protect HIV-1-infected T lymphoblastoid cells (MT4 cells) from cell-death mediated by the infection. The endpoint of the assay was calculated as the concentration of compound at which the cell viability of the culture was preserved by 50% ('50% inhibitory concentration', IC$_{50}$). The cell viability of a culture was determined by the uptake of soluble, yellow 3-[4,5-dimethylthiazol-2-yl]-2,5-diphenyltetrazolium bromide (MTT) and its reduction to a purple insoluble formazan salt. After solubilization, spectrophotometric methods were employed to measure the amount of formazan product.

MT4 cells were prepared to be in logarithmic-phase growth and a total of 2×10$^6$ cells infected with the HXB2-strain of HIV-1 at a multiplicity of 0.0001 infectious units of virus per cell in a total volume of between 200-500 microliters. The cells were incubated with virus for one hour at 37° C. before removal of virus. The cells are then washed in 0.01 M phosphate buffered saline, pH 7.2 before being resuspensed in culture medium for incubation in culture with serial dilutions of test compound. The culture medium used was RPMI 1640 without phenol red, supplemented with penicillin, streptomycin, L-glutamine and 10% fetal calf serum (GM10).

Test compounds were prepared as 2 mM solutions in dimethyl sulfoxide (DMSO). Four replicate, serial 2-fold dilutions in GM10 were then prepared and 50 microliters amounts placed in 96-well plates over a final nanomolar concentration range of 625-1.22. Fifty microliters GM10 and 3.5×10$^4$ infected cells were then added to each well. Control cultures containing no cells (blank), uninfected cells (100% viability; 4 replicates) and infected cells without compound (total virus-mediated cell death; 4 replicates) were also prepared. The cultures were then incubated at 37° C. in a humidified atmosphere of 5% CO$_2$ in air for 5 days.

A fresh solution of 5 mg/mL MTT was prepared in 0.01 M phosphate buffered saline, pH 7.2 and 20 microliters added to each culture. The cultures were further incubated as before for 2 hours. They were then mixed by pipetting up and down and 170 microliters of Triton X-100 in acidified isopropanol (10% v/v Triton X-100 in 1:250 mixture of concentrated HCl in isopropanol). When the formazan deposit was fully solubilized by further mixing, the absorbance (OD) of the cultures was measured at 540 nm and 690 nm wavelength (690 nm readings were used as blanks for artifacts between wells). The percent protection for each treated culture was then calculated from the equation:

$$\% \text{ Protection} = \frac{(OD \text{ drug treated cultures}) - (OD \text{ untreated virus control cultures})}{(OD \text{ uninfected cultures}) - (OD \text{ untreated virus control cultures})} \times 100\%$$

The IC$_{50}$ can be obtained from graph plots of percent protection versus log$_{10}$ drug concentration.

In both assays, compounds of formulas I range in activity from an IC$_{50}$ of about 0.5 to about 10000 nM or 0.5 to about 5000 nM, with preferred compounds having a range of activity from about 0.5 to about 750 nM, more preferably about 0.5 to 300 nM, and most preferably about 0.5 to 50 nM.

TABLE II

| Compound | Antiviral Assay IC$_{50}$ (µM) |
|---|---|
| I-4 | 0.0004 |

Example 15

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |

-continued

| Composition for Oral Administration (C) | |
|---|---|
| Ingredient | % wt./wt. |
| Flavoring | 0.035 ml |
| Colorings | 0.5 mg |
| Distilled water | q.s. to 100 ml |

The ingredients are mixed to form a suspension for oral administration.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compnd according to formula I wherein: (I)

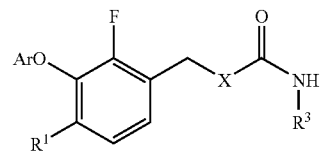

X is O or $NR^2$;

$R^1$ is halogen, $C_{1-6}$ alkyl, $C_{3-7}$ cycloalkyl, $C_{1-6}$ haloalkyl, or $C_{1-6}$ alkoxy;

$R^2$ and $R^3$ independently are (i) hydrogen or $C_{1-6}$ alkyl; (ii) $R^2$ and $R^3$ together are $(CH_2)_n$, ortho-phenylene, pyridinylene, 3,4-pyridazylene or CH=N wherein n is an integer from 2 to 4 and a nitrogen atom in said pyridinylene or 3,4-pyridazylene ring can be optionally be substituted with an oxygen; or, (iii) $R^2$ is hydrogen and $R^3$ is phenyl optionally substituted with one to 3 substituents optionally selected from the group consisting of $C_{1-6}$ alkyl, $C_{1-6}$ haloalkyl, $C_{1-6}$ alkoxy, $C_{1-6}$ haloalkoxy, halogen, cyano and nitro;

Ar is phenyl optionally substituted with one to three groups independently selected from the group consisting of selected from halogen, cyano, $C_{1-6}$ haloalkyl and $C_{1-6}$ alkyl; or, a pharmaceutically acceptable salt thereof.

2. A compound according to claim 1 wherein X is $NR^2$.

3. A compound according to claim 1 wherein X is $NR^2$ and $R^2$ and $R^3$ together are ortho-phenylene, pyridinylene or 3,4-pyridazylene.

4. A compound according to claim 3 wherein $R^1$ is bromo, chloro or $C_{1-6}$ alkyl and Ar is 3,5-disubstituted phenyl.

5. A compound according to claim 4 wherein Ar is 3-chloro-5-cyano-phenyl, dicyano-phenyl or 3-cyano-5-difluoromethyl-phenyl.

6. A compound according to claim 5 wherein $R^2$ and $R^3$ together are 2,3-pyridinylene or 3,4-pyridinylene.

7. A compound according to claim 5 wherein $R^2$ and $R^3$ together are 3,4-pyridazylene.

8. A compound according to claim 1 wherein X is $NR^2$ and $R^2$ and $R^3$ together with the atoms to which thy are attached form a 2,4-dihydro-[1,2,4]triazol-3-one optionally substituted with $C_{1-6}$ alkyl at the 5-position; $R^1$ is bromo, chloro or $C_{1-6}$ alkyl and Ar is 3,5-disubstituted phenyl.

9. A compound according to claim 1 selected from the group consisting of:
- 3-[6-Bromo-2-fluoro-3-(2-oxo-2,3-dihydro-benzoimidazol-1-ylmethyl)-phenoxy]-5-chloro-benzonitrile;
- 3-[6-Bromo-2-fluoro-3-(2-oxo-2,3-dihydro-imidazo[4,5-b]pyridin-1-ylmethyl)-phenoxy]-5-chloro-benzonitrile;
- 3-[6-Bromo-2-fluoro-3-(2-oxo-2,3-dihydro-imidazo[4,5-c]pyridin-1-ylmethyl)-phenoxy]-5-chloro-benzonitrile;
- 3-Chloro-5-[6-chloro-2-fluoro-3-(2-oxo-2,3-dihydro-imidazo[4,5-c]pyridin-1-ylmethyl)-phenoxy]-benzonitrile; and,
- 3-[6-Bromo-2-fluoro-3-(6-oxo-6,7-dihydro-imidazo[4,5-c]pyridazin-5-ylmethyl)-phenoxy]-5-chloro-benzonitrile.

10. A method for inhibiting HIV-1 reverse transcriptase in a host infected with HIV-1 comprising administering a therapeutically effective amount of a compound according to claim 1.

11. A pharmaceutical composition comprising a therapeutically effective quantity of a compound according to claim 1 and at least one carrier, excipient or diluent.

* * * * *